(12) United States Patent
Lee

(10) Patent No.: US 10,092,441 B2
(45) Date of Patent: Oct. 9, 2018

(54) SKIN CONTACT MATERIAL

(75) Inventor: Stewart Lee, Lancashire (GB)

(73) Assignee: CONVATEC LTD, Bridgewater, NJ (US)

( * ) Notice: Subject to any disclaimer, the term of this patent is extended or adjusted under 35 U.S.C. 154(b) by 664 days.

(21) Appl. No.: 14/347,966

(22) PCT Filed: Aug. 31, 2012

(86) PCT No.: PCT/GB2012/052132
§ 371 (c)(1),
(2), (4) Date: Jul. 14, 2014

(87) PCT Pub. No.: WO2013/030580
PCT Pub. Date: Mar. 7, 2013

(65) Prior Publication Data
US 2014/0323941 A1 Oct. 30, 2014

(30) Foreign Application Priority Data
Sep. 2, 2011 (GB) .................................. 1115182.6

(51) Int. Cl.
*A61F 13/00* (2006.01)
*A61M 35/00* (2006.01)
(Continued)

(52) U.S. Cl.
CPC .......... *A61F 5/443* (2013.01); *A61F 13/0253* (2013.01); *A61L 15/28* (2013.01);
(Continued)

(58) Field of Classification Search
CPC ................... A61F 5/443; A61F 13/0253; A61F 2013/00246; A61F 2013/00676; A61F 2013/00702; A61F 2013/00748; A61F 2013/00757; A61F 2013/00855; A61M 25/02; Y10T 46/24322; Y10T 46/04802
See application file for complete search history.

(56) References Cited

U.S. PATENT DOCUMENTS 3,339,546 A 9/1967 Chen et al.
3,457,919 A * 7/1969 Harbard ................ A61F 13/023
427/2.31
(Continued)

FOREIGN PATENT DOCUMENTS

EP 1815828 8/2007
EP 2442765 B1 12/2013

OTHER PUBLICATIONS

Australian Patent Application No. 2012300644 Patent Examination Report No. 2 dated May 16, 2016.
(Continued)

*Primary Examiner* — Kim M Lewis
(74) *Attorney, Agent, or Firm* — Wilson, Sonsini, Goodrich & Rosati

(57) ABSTRACT

A substrate based skin contact material formed from a hydrocolloid having a silicone based component extending over regions of the substrate surface. The adhesive is formed non-continuously over the substrate to provide areas devoid of adhesive to allow appreciable moisture transfer between the skin and substrate and improve the skin friendliness of the material during use and allow convenient removal with avoidance of skin irritation.

8 Claims, 3 Drawing Sheets

(51) Int. Cl.

| | | |
|---|---|---|
| *A61F 5/443* | (2006.01) | |
| *A61L 15/28* | (2006.01) | |
| *A61L 15/58* | (2006.01) | |
| *A61L 24/00* | (2006.01) | |
| *A61L 24/04* | (2006.01) | |
| *A61L 24/08* | (2006.01) | |
| *A61L 15/60* | (2006.01) | |
| *A61F 13/02* | (2006.01) | |
| *A61M 25/02* | (2006.01) | |
| *C09J 7/38* | (2018.01) | |
| *C09J 7/22* | (2018.01) | |
| *C09J 183/04* | (2006.01) | |

(52) U.S. Cl.
CPC ............ *A61L 15/58* (2013.01); *A61L 15/60* (2013.01); *A61L 24/0031* (2013.01); *A61L 24/046* (2013.01); *A61L 24/08* (2013.01); *A61M 25/02* (2013.01); *C09J 7/22* (2018.01); *C09J 7/38* (2018.01); *A61F 2013/0077* (2013.01); *A61F 2013/00246* (2013.01); *A61F 2013/00676* (2013.01); *A61F 2013/00702* (2013.01); *A61F 2013/00748* (2013.01); *A61F 2013/00757* (2013.01); *A61F 2013/00855* (2013.01); *A61M 2025/0266* (2013.01); *C09J 183/04* (2013.01); *Y10T 428/24322* (2015.01); *Y10T 428/24802* (2015.01)

(56) References Cited

U.S. PATENT DOCUMENTS

| | | | |
|---|---|---|---|
| 4,477,325 A | | 10/1984 | Osburn et al. |
| 4,738,257 A | | 4/1988 | Meyer et al. |
| 4,867,748 A | | 9/1989 | Samuelsen et al. |
| 4,882,377 A | | 11/1989 | Sweet et al. |
| 5,009,648 A | * | 4/1991 | Aronoff .................. A61F 5/445 604/332 |
| 5,051,259 A | * | 9/1991 | Olsen ...................... A61F 5/445 424/443 |
| 5,622,711 A | | 4/1997 | Chen |
| 6,206,864 B1 | * | 3/2001 | Kavanagh ............... A61F 5/448 604/332 |
| 2007/0179461 A1 | * | 8/2007 | Sambasivam .......... A61L 15/58 604/336 |
| 2009/0069764 A1 | * | 3/2009 | Burlot .................. A61L 24/001 604/345 |
| 2009/0312685 A1 | * | 12/2009 | Olsen ...................... A61F 5/443 602/54 |

OTHER PUBLICATIONS

New Zealand Patent Application No. 623093 Further Examination Report Acceptance dated Apr. 22, 2016.
New Zealand Patent Application No. 623093 Further Examination Report dated Mar. 17, 2016.
Chinese Patent Application No. 201280053745.3 Office Action dated Sep. 26, 2016.
Russian Patent Application No. 2014112702 Official Action dated Aug. 23, 2016.
Chinese Patent Application No. 201280053745.3 Office Action dated Jun. 22, 2017.
Russian Patent Application No. 2014112702/15 Office Action dated Jun. 2017.
Russia Patent Application No. 2014112702 Office Action dated Nov. 8, 2017.

* cited by examiner

SECTION B - B

SECTION A - A

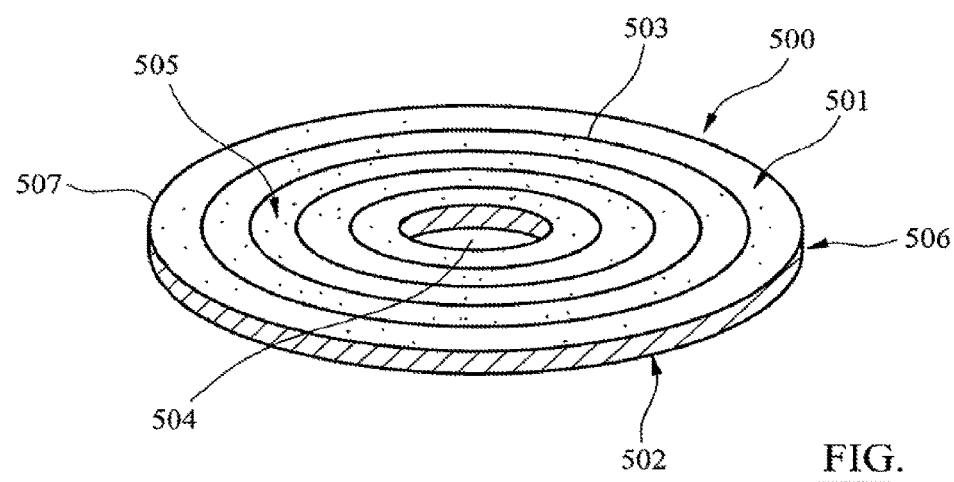
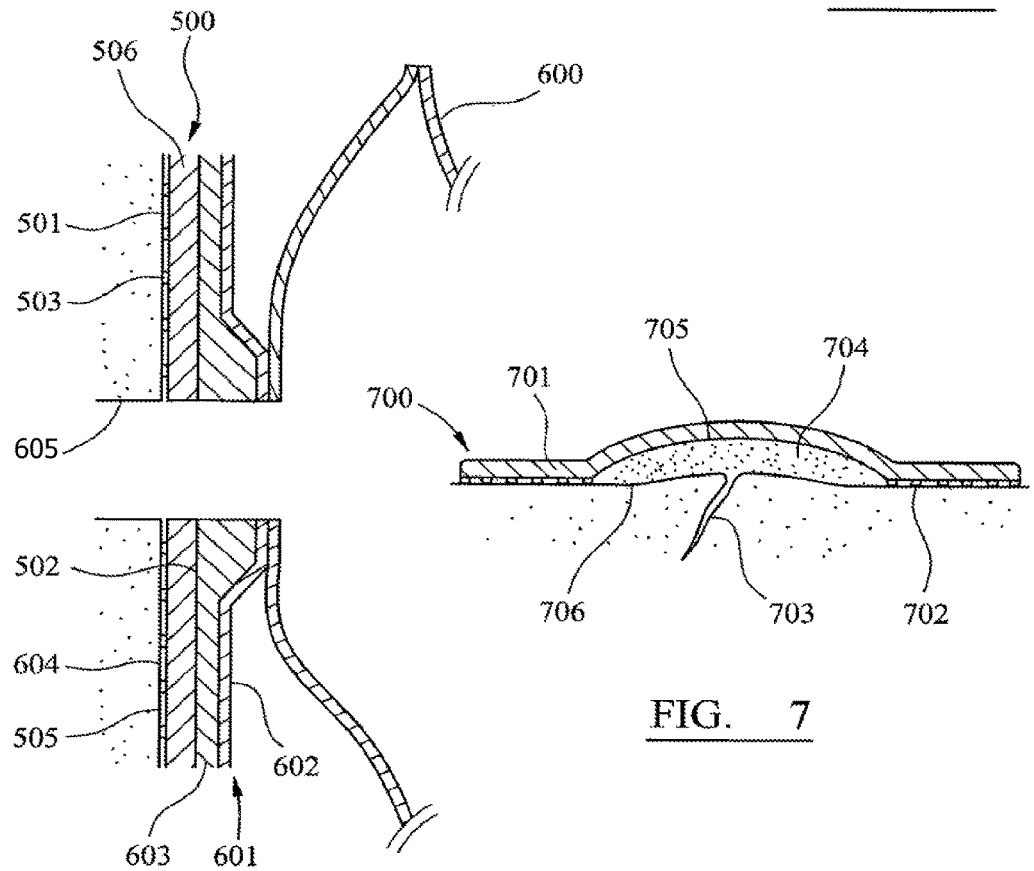

SKIN CONTACT MATERIAL

CROSS-REFERENCE

This application is a U.S. National Phase of PCT/GB2012/052132, filed Aug. 31, 2012, which claims the benefit of priority of GB 1115182.6, filed Sep. 2, 2011, each of which is incorporated herein by reference in their entirety.

BACKGROUND OF THE INVENTION

The present invention relates to a skin contact material for positioning against a human or animal skin and in particular, although not exclusively, to a material suitable for ostomy use, wound care and as a medical dressing and adhesive.

Self-adhering skin contact materials find widespread use in the medical field and in particular with ostomy appliances. Initially, medical grade pressure-sensitive adhesives, typically formed from an acrylic, were used to adhere appliances to the peristomal skin of a patient. More recently, moisture absorbing, and in particular hydrocolloid containing, skin barrier materials have emerged as more suitable skin contact materials. These materials absorb moisture from the skin and allow the skin to breathe whilst being sufficiently tacky for good skin adhesion but being easily peeled away without irritating or damaging the skin.

Skin friendly adhesive barrier materials are disclosed in U.S. Pat. No. 3,339,546; U.S. Pat. No. 4,477,325; U.S. Pat. No. 4,738,257 and U.S. Pat. No. 4,867,748.

However, hydrocolloid based substrates may not possess the required adhesive characteristics for certain skin contact applications and an additional adhesive may be required. The problem with medical grade adhesives is that they tend to be skin irritants following extended use. In particular, and as a generalisation, they do not allow the same level of moisture transfer with the skin.

What is required therefore is a medical grade skin contact material for use as a barrier layer and/or a means of attaching appliances to the skin that comprise the required adhesive properties whilst allowing moisture transfer with the skin.

Accordingly, the inventors provide a substrate based skin contact material preferably formed from a hydrocolloid having a silicone based adhesive component extending over regions of the substrate surface. The adhesive is formed non-continuously over the hydrocolloid so as to provide areas of the hydrocolloid that are devoid of the silicone adhesive. Accordingly, with the material in contact with the skin, adhesion is provided via the silicone adhesive whilst the areas of exposed hydrocolloid are capable of moisture transfer so as to significantly improve the skin friendliness of the material during use and allow the material to be readily removed from the skin without causing irritation.

BRIEF SUMMARY OF THE INVENTION

According to a first aspect of the present invention there is provided a skin contact material for positioning against human or animal skin, the material comprising: a hydrocolloid substrate having a first surface intended to be positioned against the skin and a second surface intended to be facing away from the skin; a silicone adhesive layer provided on the first surface and intended to be positioned in contact with the skin to adhere the material to the skin, the silicone adhesive layer being non-continuous over the first surface such that areas of the first surface are not concealed by the silicone adhesive layer, the areas capable of positioning directly adjacent and/or in contact with the skin.

The hydrocolloid substrate may comprise a synthetic or natural hydrocolloid, such as a hydrocolloid derived from natural sources. The hydrocolloid may comprise anyone or a combination of a gum, a cellulose or cellulose derivative, an alginate or a starch.

Optionally, the hydrocolloid comprises gelatine or pectin. Optionally, the hydrocolloid comprises a carboxymethylcellulose in a polyisobutylene matrix. Alternatively, the substrate may be non-hydrocolloid based and may comprise low density polyethylene, high density polyethylene, polypropylene, polyester or a silicone based material. Alternatively the substrate could be a composite of two or more different materials including polymers and hydrocolloids.

Preferably, the silicone adhesive comprises a two part catalysed, low temperature curing silicone elastomer. As will be appreciated, the silicone adhesive may be formed as a composite of a plurality of different silicones and/or silicone based materials.

Optionally, the skin contact material may be provided as a sheet or roll from which a user or medical practitioner may cut the desired shape and size. Moreover, the hydrocolloid substrate may comprise a thickness in the range 0.5 to 5.0 mm.

As indicated, the enhanced skin friendliness of the present material is provided by layering the silicone adhesive upon the substrate at discrete regions so as to provide areas of exposed substrate for positioning in contact with the skin. Accordingly, the silicone adhesive may be formed as lines or dots on the skin contact surface of the substrate.

Where the adhesive layer is formed as individual dots, flecks or marks, the pattern created by these dots may be uniform across the surface of the substrate. Alternatively, the pattern may change over the substrate surface and the material may comprise different patterns at different regions over the substrate. Where the adhesive layer comprises lines or ridges extending over the substrate, these lines may extend in different directions where the spacing between the lines or ridges is the same or variable across the substrate surface. Optionally, the lines may create a square, rectangular or circular grid pattern. Preferably, for ostomy applications, the silicone adhesive is bonded to the substrate and takes the form of concentric circles extending around a central aperture extending through the substrate.

According to a second aspect of the present invention there is provided a medical dressing comprising a skin contact material as described herein. According to a third aspect of the present invention there is provided a stoma gasket comprising a skin contact material as described herein. According to a fourth aspect of the present invention there is provided a medical adhesive pad, tape or sheet comprising a skin contact material as described herein. According to a fifth aspect of the present invention there is provided a skin barrier pad for positioning about a stoma comprising a skin contact material as described herein. According to a sixth aspect of the present invention there is provided an ostomy bag comprising a skin contact material as described herein.

According to a seventh aspect of the present invention there is provided a skin contact material for positioning against human or animal skin, the material comprising: a substrate having a first surface intended to be positioned against the skin and a second surface intended to be facing away from the skin, the substrate comprising any one or a combination of a hydrocolloid, a low density polyethylene, a high density polyethylene, a polypropylene, a polyester or a silicone based material; a silicone adhesive layer provided on the first surface and intended to be positioned in contact with the skin to adhere the material to the skin, the silicone adhesive layer being non-continuous over the first surface such that areas of the first surface are not concealed by the silicone adhesive layer, the areas capable of positioning directly adjacent and/or in contact with the skin.

BRIEF DESCRIPTION OF THE DRAWINGS

A specific implementation of the present invention will now be described, by way of example only, and with reference to the accompanying drawings in which:

FIG. 5 is a perspective view of a stoma gasket formed from the skin contact material according to a specific implementation;

FIG. 6 contains a cross sectional side view of the stoma gasket at an adhesive ring of FIG. 5 secured in position against a patient's skin and in contact with a flange of an ostomy bag;

FIG. 7 is a cross sectional side view of the skin contact material used as a wound dressing adhesive to maintain a dressing in position over a wound at the skin.

DETAILED DESCRIPTION OF THE INVENTION

Figure 1:
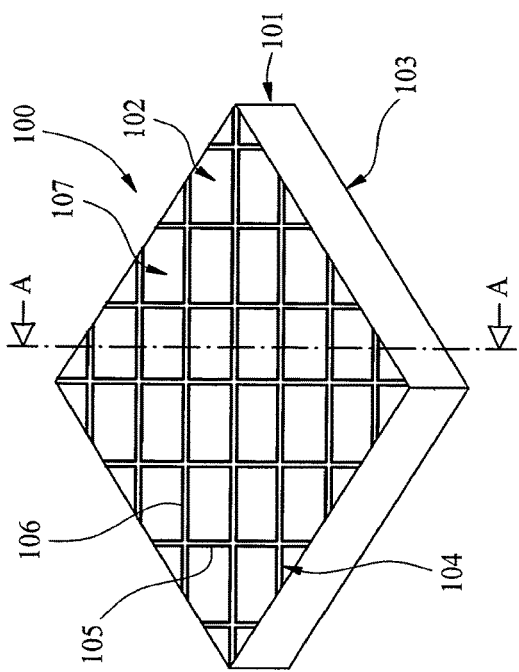
FIG. 1 is perspective view of a skin contact material having a substrate and an adhesive component bonded to one face of the substrate according to the specific implementation.
Figure 2:
FIG. 2 is a cross section to A-A of FIG. 1.

Referring to FIGS. 1 and 2, the skin contact material 100 comprises a substrate 101 having a first surface 102 intended to be facing the skin and an apposed second surface 103 intended to be facing away from the skin. An adhesive layer 104 is provided on the surface 102 and according to the specific implementation, layer 104 comprises a rectangular grid pattern formed by perpendicular aligned ridges 105, 106.

Adhesive layer 104, formed from the narrow ridges 105, 106 is regarded as 'discontinuous' over surface 102 such that the adhesive 104 does not coat completely surface 102 and there is provided regions 107 that are devoid of adhesive 104 with regions 107 being exposed substrate 102. The rectangular grid pattern formed by ridges 105, 106 is uniform across surface 102 such that the space between ridges 105, 106 is equal in the respective directions across substrate surface 102. According to the specific implementation, the thickness of substrate 101 is in range 0.5 to 5.0 mm. The distance by which ridges 105, 106 extend from surface 102 is a small percentage of this thickness and may be of the order of 0.01 mm.

Figure 3:
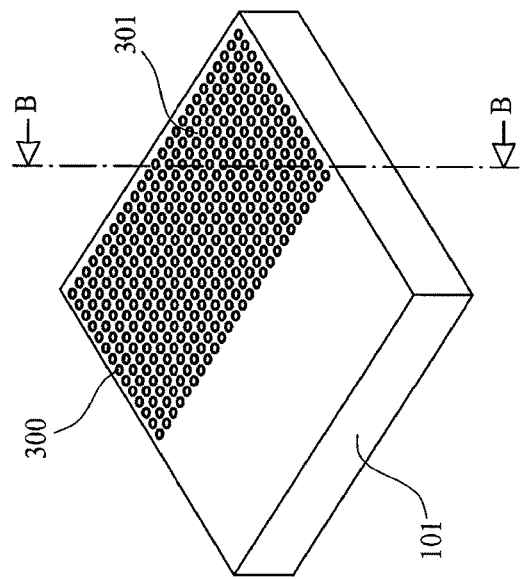
FIG. 3 is a perspective view of a further specific implementation of the skin contact material of FIG. 1.
Figure 4:
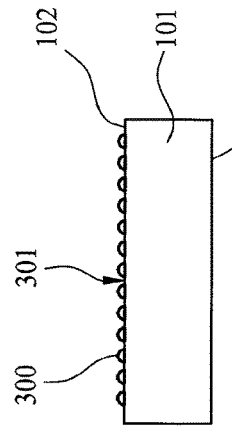
FIG. 4 is a cross section through B-B to FIG. 3.

FIGS. 3 and 4 illustrate a further embodiment of the skin contact material of FIGS. 1 and 2. According to the further embodiment, the adhesive layer is formed as a regular repeating array of nodes or bumps 300. The bumps 300 are separated from one another by a regular or uniform discreet separation distance such that the skin contact surface 102 of substrate 101 is exposed at spacings 301 between the bumps 300.

The material of the embodiment of FIGS. 1 to 4 is suitable for use as a medical grade skin contact material and in particular a material for adherence to the skin of colostomy, ileostomy and urostomy appliances. The material is also suitable for adherence to the skin of patient monitoring appliances, prosthetics and wound dressings.

Specifically with regard to ostomy applications, FIG. 5 illustrates a specific embodiment of the skin contact material 500 formed as an annular disc suitable for use as a skin contact stoma gasket. The skin contact material 500 comprises a central aperture or bore 504 extending through skin contact material 500. Skin contact material 500 comprises a substrate 506 having a skin contact surface 501 and opposed surface 502 intended to be facing away from the skin. An adhesive layer 503 is provided on the surface 501 and is formed as a series of concentric circles extending between central bore 504 and parameter edge 507. The concentric circles of the adhesive layer 503 are spaced apart from one another and therefore formed as discreet ridges separated by regions 505 of exposed substrate surface 501.

FIG. 6 illustrates the skin contact material 500 of FIG. 5 secured in position at the peristomal skin 604. The adhesive ridges of the adhesive layer 503 are positioned in contact with the peristomal skin 604 such that regions 505 are in a position very close to or in direct contact with skin 604 so as to provide moisture transfer between skin contact material 500 and skin 604. That is, moisture is actively transferred from skin 604 and into material 500 via regions 505. This would otherwise not be possible if adhesive layer 503 extended continuously over skin contact surface 501.

An ostomy bag 600 comprises a flange 601 formed from a solid support 602 that supports an attachment flange 603. Bag 600 is secured to the skin 604 indirectly by mating attachment 603 with the external facing surface 502 of skin contact material 500. Central bore 504 of skin contact material 500 is appropriately sized to fit around stoma 605 and allow the free passage of excreted matter into bag 600. The ostomy bag 600 and the skin contact material 500 may be readily removed from the peristomal skin 604 by simply pilling-away the skin contact material 500.

FIG. 7 illustrates a further use of the present skin contact material as a wound dressing. The wound dressing 700 comprises a substrate 701 and an adhesive layer 702 incompletely formed across the skin contact surface of substrate 701. According to the further embodiment, adhesive layer 702 may be formed at an outer perimeter region of the substrate so as to provide a central region 705 that is devoid of adhesive 702.

Alternatively, adhesive layer 702 may extend across the entire skin facing surface of substrate 701 but importantly comprising regular repeating regions that are devoid of the adhesive layer. The adhesive patch 700 is configured to retain a second wound dressing material 704 in contact with the skin 706 surrounding the region of a wound 703. Due to the moisture transfer capability of substrate 701, the skin 706 at the region in contact with the pad 700, is allowed to breathe and does not become irritated by this contact.

According to further embodiments, the silicon adhesive layer 104, 300, 503, 702 may also be provided on the second surface of the substrate 103, 502 intended to be facing away from the skin. This second opposed adhesive layer may have the same or a different configuration to the skin contact adhesive layer on the first surface. Also, this second and opposed adhesive layer may have a uniform configuration across the second surface 103, 502 or the configuration may be different at different regions on surface 103, 502 as described with references to the first adhesive layer detailed in FIGS. 1 to 7.

Figure 8:
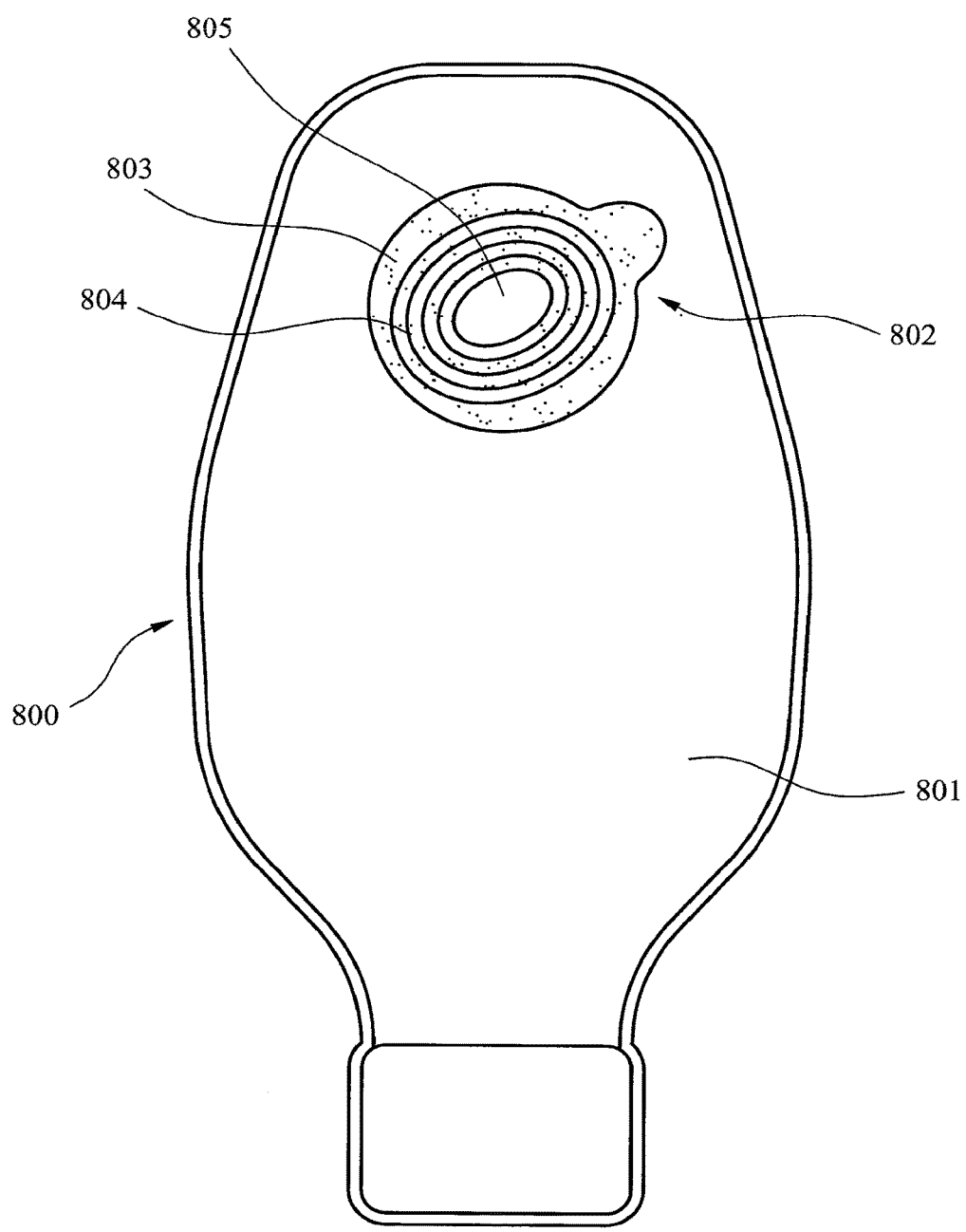
FIG. 8 is a side view of an ostomy bag having a flange comprising the skin contact material according a specific implementation.

FIG. 8 illustrates an ostomy bag 800 having an internal chamber 801 to receive excreted matter. An attachment flange 802 provides an interface between the chamber 801 and a stoma whilst providing a means of attachment of the bag 800 to the peristomal skin. The present skin contact material is formed as a permanent or releasable part of flange 802 and extends around a central aperture 805 for positioning around the stoma. Flange 800 comprises a substrate 803 with moisture transfer characteristics as described with reference to FIGS. 1 to 7. A silicone adhesive layer 804, as described herein, is formed as discrete concentric circles on the skin facing side of flange 802 and extends around the central aperture 805 as described with reference to FIG. 5.

According to further specific implementations the substrate may be non-hydrocolloid based and may comprise medical grade polymers such as polyalkylenes, polyesters and/or silicone based materials.

According to a first example the substrate may comprise a low density polyethylene. Suitable low density polyethylene materials include those available from Dow Corning, MI, USA under the product range Dow™ LDPE.

According to a second example the substrate may comprise a high density polyethylene. Suitable materials include those available from Dow Corning, MI, USA under the product range Dow™ HDPE or materials under the product range Eraclene™ HDPE available from Polimeri Europa, ENI Rome, Italy.

According to a third example the substrate may comprise a polypropylene material. Suitable materials include those available from Westlake Plastics Company, PA, USA under the product range Propylux™ HS.

According to a fourth example the substrate may comprise a polyester material. Suitable materials include polyesters available from Bayer MaterialScience LLC, PN, USA under the product range Texin™ RxHM125.

According to a fifth example, the substrate may comprise a silicone based material. Suitable materials include those available from Dow Corning, MI, USA under the product range Silastic™ and the Class VI Elastomers under the product range C-6.

As will be appreciated, the different types of substrate according to the further examples are bondable to the adhesive layer according to conventional bonding techniques and processes as described with reference to the previous embodiments.

The invention claimed is:

1. A skin contact material for positioning against human or animal skin, the material comprising:
a hydrocolloid substrate having a first surface intended to be positioned against the skin and a second surface intended to be facing away from the skin;
a two part catalysed, low temperature curing silicone adhesive layer coated on the first surface configured to contact and adhere the material to the skin, the two part catalysed, low temperature curing silicone adhesive layer being non-continuous over the first surface such that areas of the first surface are not concealed by the two part catalysed, low temperature curing silicone adhesive layer, the non-concealed areas of the first surface configured for positioning in contact with the skin to allow moisture transfer between the skin and the hydrocolloid substrate; wherein the skin contact material comprises a central aperture extending through the substrate and the silicone adhesive layer; and the silicone adhesive layer is coated on the first surface as at least four concentric circles extending between the central aperture and a parameter edge of the substrate, the concentric circles spaced apart from one another to form discrete ridges separated by the areas of the first surface not concealed by the silicone adhesive layer.

2. The material as claimed in claim 1 wherein the hydrocolloid substrate comprises any one or a combination of the following set of:
a gum;
a cellulose;
cellulose derivative;
an alginate;
a starch.

3. The material as claimed in claim 1 further comprising gelatine or pectin.

4. The material as claimed in claim 1 wherein the two part catalysed, low temperature curing silicone adhesive layer is a composite and comprises a plurality of different silicones and/or silicone based materials.

5. The material as claimed in claim 1 wherein the hydrocolloid substrate comprises a thickness in a range of 0.5 to 5.0 mm.

6. A stoma gasket comprising a skin contact material according to claim 1.

7. A stoma skin barrier pad for positioning around a stoma comprising a skin contact material according to claim 1.

8. An ostomy bag comprising a skin contact material according to claim 1.

* * * * *